United States Patent

Steppan et al.

[11] Patent Number: 5,200,299
[45] Date of Patent: Apr. 6, 1993

[54] QUINOLINE AND ACRIDINE COMPOUNDS EFFECTIVE AS PHOTOINITIATORS AND CONTAINING POLYMERIZABLE (METH)ACRYLOYL SUBSTITUENTS

[75] Inventors: Hartmut Steppan; Hans-Dieter Frommeld, both of Wiesbaden, Fed. Rep. of Germany

[73] Assignee: Hoechst Aktiengesellschaft, Frankfurt am Main, Fed. Rep. of Germany

[21] Appl. No.: 454,199

[22] Filed: Dec. 21, 1989

[30] Foreign Application Priority Data

Dec. 22, 1988 [DE] Fed. Rep. of Germany ....... 3843205

[51] Int. Cl.$^5$ .................... G03F 7/031; C07D 215/18; C07D 219/02; C07D 215/12
[52] U.S. Cl. .................................. 430/281; 430/920; 522/904
[58] Field of Search ................ 430/281, 920; 546/102, 546/104, 173, 174, 175, 79; 522/904

[56] References Cited

U.S. PATENT DOCUMENTS

| | | | |
|---|---|---|---|
| 3,751,259 | 8/1973 | Bauer et al. | 96/115 P |
| 4,272,609 | 6/1981 | Klüpfel | 430/288 |
| 4,444,868 | 4/1984 | Ichimura | 430/285 |
| 4,587,200 | 5/1986 | Tamoto et al. | 430/281 |
| 4,659,645 | 4/1987 | Frommeld et al. | 430/175 |
| 4,737,445 | 4/1988 | Frommeld et al. | 430/281 |
| 4,985,564 | 1/1991 | Kakumaru et al. | 546/104 |

FOREIGN PATENT DOCUMENTS

| | | | |
|---|---|---|---|
| 51-004181 | 1/1976 | Japan | 546/102 |
| 58-24562 | 2/1983 | Japan | 546/174 |

OTHER PUBLICATIONS

Journal Of Polymer Science: Part A: Polymer Chemistry, vol. 25, 3063–3077 (1987).

*Primary Examiner*—Cynthia Hamilton
*Attorney, Agent, or Firm*—Foley & Lardner

[57] ABSTRACT

Compounds of the general formula I

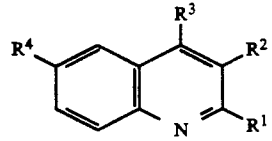

are described in which
$R^1$ is a group of the formula

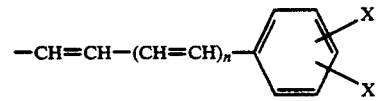

and
$R^2$ is a hydrogen atom or a methyl group, or
$R^1$ and $R^2$ jointly form an optionally substituted 5- or 6-membered ring,
$R^3$ is a hydrogen atom, a methyl group or an optionally substituted phenyl group,
$R^4$ is a hydrogen or halogen atom, a methyl group, an optionally substituted benzoyl group or a group of the formula

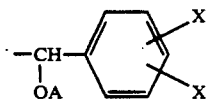

n is zero or 1,
X is a hydrogen or chlorine atom, an alkyl group containing 1 to 4 carbon atoms or one of the groups OA, CH$_2$OA, CH$_2$NHA or C$_2$H$_4$OA, and
A is an acryloyl or methacryloyl group,
the compounds containing in each case at least one group A. The compounds are suitable for the production of photoresists and printing plates as diffusion-resistant photoinitiators in photopolymerizable mixtures.

13 Claims, No Drawings

QUINOLINE AND ACRIDINE COMPOUNDS EFFECTIVE AS PHOTOINITIATORS AND CONTAINING POLYMERIZABLE (METH)ACRYLOYL SUBSTITUENTS

BACKGROUND OF THE INVENTION

The invention relates to novel photopolymerizable compounds, to a photopolymerizable mixture containing said compounds, and also to a photopolymerizable copying material comprising a coating base and a photopolymerizable coating which is composed of the mixture.

DE-C-2,027,467 discloses photopolymerizable mixtures which contain polymeric binders, polymerizable compounds and derivatives of acridine and phenazine as photoinitiators. Some of the representatives of this class of compound, for example 9-phenylacridine, are notable for high photosensitivity. The preferred representatives have the disadvantage that they tend to migrate out of the photopolymerizable coatings and, in particular, out of photocured photoresist coatings in certain kinds of treatment baths, for example acidic electroplating baths, and produce a troublesome yellow coloration therein.

EP-A-11,786 and 220,589 disclose corresponding mixtures which contain certain quinoline derivatives as photoinitiators. These mixtures, too, which are photosensitive like the above-mentioned mixtures, suffer from the same disadvantages.

In the photocured state, the known photopolymerizable materials often have an inadequate mechanical strength and hardness for some purposes. This is particularly true in the applications as solder masks, as permanent resist and as lithographic printing plates.

SUMMARY OF THE INVENTION

Accordingly, it is an object of the present invention to provide photopolymerizable compounds and mixtures which yield copying materials having as good photosensitivity and image reproduction as the preferred known mixtures, but in which the photoinitiators exhibit a lesser tendency to migrate out of the photopolymerizable or photopolymerized coating and the photocured coatings have a higher mechanical resistance and strength.

In accordance with one aspect of the present invention, there is provided a compound of the general formula I

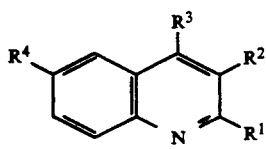

in which
$R^1$ is a group of the formula

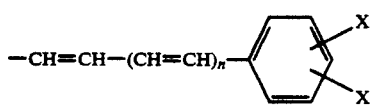

and
$R^2$ is a hydrogen atom or a methyl group, or $R^1$ and $R^2$ jointly form an optionally substituted 5- or 6-membered carbocyclic ring,
$R^3$ is a hydrogen atom, a methyl group or an optionally substituted phenyl group,
$R^4$ is a hydrogen or halogen atom, a methyl group, an optionally substituted benzoyl group or a group of the formula

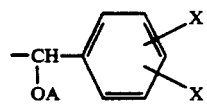

n is zero or 1,
X is a hydrogen or chlorine atom, an alkyl group containing 1 to 4 carbon atoms or one of the groups OA, $CH_2OA$, $CH_2NHA$ or $C_2H_4OA$, where a plurality of Xs may be identical or different from one another, and
A is an acryloyl or methacryloyl group,
the compounds in each case containing at least one group A.

In accordance with another aspect of the present invention, there is provided a photopolymerizable mixture which comprises:
 a) a polymeric binder,
 b) a polymerizable compound having at least one terminal olefinic double bond and a boiling point above 100° C. at normal pressure, and
 c) A N-heterocyclic compound as photoinitiator,
wherein the N-heterocyclic compound is a compound of the above general formula I.

In accordance with yet another aspect of the present invention, there is provided a photopolymerizable copying material which has a coating base and a photopolymerizable coating applied thereto which is composed of the above defined photopolymerizable mixture.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

The compounds according to the invention are novel. They are prepared by esterification of the hydroxyl compounds on which they are based with activated derivatives, for example anhydrides or chlorides, of acrylic and methacrylic acid Some of the hydroxyl compounds are known, and some of them are prepared by analogy with known processes. 9-(4-Hydroxyphenyl)acridine is known; 2-(4-hydroxystyryl)quinoline can be reacted, for example by condensation with 1 mole of quinaldine with 1 mole of 4-hydroxybenzaldehyde in acetic anhydride with the addition of a few drops of concentrated sulfuric acid, to form 2-(4-acetoxystyryl)quinoline. From this the free hydroxy compound is obtained by hydrolysis with alcoholic potassium hydroxide solution. Instead of quinaldine, other quinoline derivatives containing activated methylene groups, for example 9-phenyl-2,3-dihydro-1H-cyclopenta[b]quinoline, may be used. In this case the intermediate obtained is 3-(4-acetoxybenzylidene)-9-phenyl-2,3-dihydro-1H-cyclopenta[b]quinoline which can subsequently be hydrolyzed. This and other suitable compounds are described in EP-A-220,589. Instead of p-hydroxybenzaldehyde or p-hydroxycinnamaldehyde, the corresponding aromatic dihydroxy compounds may be used.

Compounds of the formula I in which $R^1$ and $R^2$ form a benzene ring are prepared by condensing diphenylamine or its simple substitution products, for example 3-methyldiphenylamine or a chlordiphenylamine with benzoic acid or simple benzoic acid derivatives, for example tert-butylbenzoic acid, benzophenone-4-carboxylic acid, diphenyl-4-carboxylic acid, 4-aminomethylbenzoic acid or terephthalic acid in a suitable reaction medium such as polyphosphoric acid at about 150°-200° C. to form a 2,7-dibenzoyl-9-phenylacridine derivative. Then the carbonyl groups of the optionally substituted benzoyl groups are reduced, for example with sodium boranate, to the —CHOH— group.

Of the compounds according to the invention, those are preferred in which $R^1$ and $R^2$ are joined to form a ring which may be aromatic or partially hydrogenated, but is preferably a benzene ring. $R^3$ is preferably a phenyl group which carries, in particular, one or more substituents X. One substituent is preferably in the 4-position. If $R^1$ and $R^2$ together denote a benzene ring, the latter is preferably substituted, in particular in the 2-position of the acridine nucleus formed therewith. Possible substituents are especially those having the meaning of $R^4$. Acridine compounds in which the 2- and 7-positions carry such substituents are particularly advantageous since they have a strongly reduced diffusion capability analogously to the compounds described in the simultaneously filed Patent Application P 3,843,204.8, corresponding to U.S. application Ser. No. 07/454,198. The compounds according to the invention may contain one or more, in general 1 to 3, acryloyl or methacryloyl groups, compounds containing two polymerizable groups being particularly advantageous because of their crosslinking action.

Examples of suitable compounds according to the invention are 2-[4-(4-acryloyloxyphenyl)butadienyl]-quinoline, 3-(3,4-bisacryloyloxybenzylidene)-9-methyl-2,3-dihydro-1H-cyclopentab]quinoline, 3-(2,4-bismethacryloyloxybenzylidene)-7-chloro-9-(2-chlorophenyl)-2,3-dihydro-1H-cyclopenta[b]quinoline, 2,7-dimethyl-9-(4-acryloylaminomethylphenyl)acridine, 2,7-bis(α-methacryloyloxy-4-tert-butylbenzyl)-9-(4-tert-butylphenyl)acridine, 2,7-bis(4-acryloyloxymethylbenzoyl)-9-(4-acryloyloxymethylphenyl)acridine, 9-(4-methacryloyloxyethylphenyl)acridine and 2,7-bis(α-methacryloyloxybenzyl)-9-phenylacridine.

The quantitative proportion of the compounds of formula I in the mixture according to the invention is in general about 0.01 to 10, preferably 0.1 to 5% by weight, based on the non-volatile constituents.

Suitable polymerizable compounds for the purposes of the invention are known and are described, for example, in U.S. Pat. Nos. 2,760,863 and 3,060,023.

Preferred examples are acrylates and methacrylates of mono- or polyhydric, preferably at least dihydric alcohols, such as ethylene glycol diacrylate, polyethylene glycol dimethacrylate, acrylates and methacrylates of trimethylolethane, trimethylolpropane, pentaerythritol and dipentaerythritol and of polyhydric alicyclic alcohols or N-substituted acrylic and methacrylic acid amides. Advantageously, reaction products of mono- or diisocyanates with partial esters of polyhydric alcohols are also used. Monomers of this type are described in DE-A-2,064,079, 2,361,041 and 2,822,190. The quantitative proportion of monomers in the coating is in general about 10 to 80, preferably 20 to 60% by weight.

The mixture contains, in addition, a polymeric binder. A multiplicity of soluble organic polymers can be used as binder.

As examples, mention may be made of polyamides, polyvinyl esters, polyvinyl acetals, polyvinyl ethers, epoxy resins, polyacrylic acid esters, polymethacrylic acid esters, polyesters, alkyd resins, polyacrylamide, polyvinyl alcohol, polyethylene oxide, polydimethacrylamide, polyvinyl pyrrolidone, polyvinylmethylformamide, polyvinylmethyl acetamide and also copolymers of the monomers which form the homopolymers listed.

Furthermore, natural substances or modified natural substances, for example gelatin and cellulose ethers, are possible as binders.

The use of binders which are water-insoluble but are soluble, or at least swellable, in aqueous alkali solutions is particularly advantageous since coatings containing such binders can be developed with the preferred aqueous alkaline developers. Such binders may contain, for example, the following groups: —COOH, $PO_3H_2$, —$SO_3H$, —$SO_2NH$—, —$SO_2$—NH—$SO_2$— and —$SO_2$—NH—CO—.

As examples thereof, mention may be made of maleate resins, polymers of β-(methacryloyloxy)ethyl N-(p-tolylsulfonyl)carbamate and copolymers of the latter and similar monomers with other monomers and also vinyl acetate/crotonic anhydride and styrene/maleic anhydride copolymers. Alkyl methacrylate/methacrylic acid copolymers and copolymers of methacrylic acid, higher alkyl methacrylates and methyl methacrylate and/or styrene, acrylonitrile etc., such as are described in DE-A-2,064,080 and 2,363,806, are preferred.

The quantity of binder is in general about 20 to 90, preferably 40 to 80% by weight of the constituents of the coating.

Depending on the planned application and depending on the desired properties, the photopolymerizable mixtures may contain diverse substances as additives.

Examples are: inhibitors for preventing thermal polymerization of the monomers; hydrogen donors; substances which modify the spectral photosensitivity of coatings of this type; dyestuffs; colored and colorless pigments; color formers; indicators; and plasticizers, for example polyglycols or esters of p-hydroxybenzoic acid.

These constituents are advantageously chosen in a manner such that they have as little absorption as possible in the actinic radiation range which is important for the initiation process.

For the purpose of this description, actinic radiation shall be understood to mean any radiation whose energy is equivalent at least to that of shortwave visible light. Longwave UV radiation and also electron radiation, x-ray radiation and laser radiation are suitable.

The photopolymerizable mixture may be used for a wide variety of applications, for example to produce safety glass, lacquers which are cured by light or corpuscular beams, for example electron beams, in the field of dentistry and, in particular, as photosensitive copying material in the field of reproduction.

The detailed description of the invention is restricted to the latter field of application, but the invention is not restricted thereto. As possible applications in this field, mention may be made of copying materials for the photomechanical production of print forms for letterpress printing, lithographic printing, gravure printing, screen printing, of relief copies, for example production of texts in Braille, of single copies, tanned images, pigment images, etc. Furthermore, the mixtures may be used for the photomechanical production of etch resist, for example for manufacturing nameplates, printed circuits and for chemical milling. The mixtures according to the invention are particularly important as copying materials for the photomechanical production of lithographic print forms and for the photoresist techniques.

For the said application purposes, the mixture can be utilized commercially in the form of a liquid solution or dispersion, for example as a photoresist solution, which is applied by the user himself to an individual base, for example for chemical milling, for the production of printed circuits, of screen printing stencils and the like. The mixture may also take the form of a solid photosensitive coating on a suitable base in the form of a storable precoated photosensitive copying material, for example for the production of print forms. It is also suitable for the production of dry resist.

It is in general beneficial to largely exclude the mixtures from the influence of atmospheric oxygen during the photopolymerization. If the mixture is used in the form of thin copying coatings, it is advisable to apply a suitable top coat which has low permeability to oxygen. The latter may be self-supporting and may be peeled off before the copying coating is developed. Polyester films, for example, are suitable for this purpose. The top coat may also be composed of a material which dissolves in the developer liquid or may be removed at least at the non-cure points during development. Suitable materials for this purpose are, for example, waxes, polyvinyl alcohol, polyphosphates, sugar etc.

Suitable coating bases for copying materials produced with the mixture according to the invention are, for example, aluminum, steel, zinc, copper and plastic films, for example made of polyethylene terephthalate or cellulose acetate, and also screen printing bases such as perlon gauze.

The photosensitive materials using the mixture according to the invention are produced in a known manner.

Thus, the mixture can be taken up in a solvent and the solution or dispersion may be applied by pouring, spraying, immersion application with rollers, etc. as a film to the base provided and then dried. Thick coatings (for example of 250 μm and over) are advantageously produced by extrusion or pressing as a self-supporting film which is then possibly laminated onto the base. In the case of dry resist, solutions of the mixture are applied to transparent temporary bases and dried. The photosensitive coatings (thickness approximately between 10 and 100 μm) are then laminated onto the desired final substrate, initially by lamination together with the temporary base.

The processing of the materials is carried out in a known manner. For the purpose of development, they are treated with a suitable developer solution, preferably a weakly alkaline aqueous solution, in which process the unexposed portions of the coating are removed and the exposed regions of the copying coating remain behind on the base.

The copying materials according to the invention are notable for a low loss in photosensitivity during storage. This advantage is effected apparently by a higher resistance to diffusion of the initiators in the photopolymerizable coating compared with unsubstituted 9-phenylacridine. The initiators do not migrate, or migrate to a substantially lesser extent than known initiators, out of the photocured coating. After exposure the materials yield coatings with higher mechanical strength and resistance to abrasion, for example, under pressure.

Examples of the mixture according to the invention are given below. Here the preparation of compounds of the formula I are first described. Then application examples for using the photopolymerizable mixtures are described.

In the examples, parts by weight (pbw) and parts by volume (pbv) are in the ratio of g to ccm. Unless otherwise specified, percentage and quantity ratios are understood in units of weight.

PREPARATION EXAMPLES

1.

2,7-Dimethyl-9-(4-acryloylaminomethylphenyl)acridine 197 pbw (1 mol) of 4,4'-dimethyldiphenylamine and 151 pbw (1 mol) of 4-aminomethylbenzoic acid were heated at 200° C. for 1 hour in 5,000 pbw of polyphosphoric acid. After cooling, water and ammonia were added to the reaction mixture, the 2,7-dimethyl-9-(4-aminomethylphenyl)acridine was filtered off by suction, purified and dried (m.p. 220° C.).

The product was acrylated with acryloyl chloride and triethylamine in acetone.

2. 2,7-Bis(α-methacryloyloxybenzyl)-9-phenylacridine 1 pbw of diphenylamine and 15 pbw of polyphosphoric acid were heated to 100° C. while stirring. After adding 2.5 pbw of benzoic acid, the mixture was heated at 200° C. for 45 minutes. After cooling to 100° C., the mixture was poured into 70 pbw of water, the 2,7-dibenzoyl-9-phenylacridine was filtered off and purified (m.p. 210° C.).

1 pbw of 2,7-dibenzoyl-9-phenylacridine was suspended in 4 pbw of ethanol and reduced at 20°-50° C. with 0.1 pbw of sodium boranate (in portions). After 24 hours, the reaction product 2,7-bis(α-hydroxybenzyl)-9-phenylacridine was precipitated with water, purified and dried (m.p. above 280° C.).

1 pbw of 2,7-bis(α-hydroxybenzyl)-9-phenylacridine was suspended in 4 pbw of acetone and heated under reflux for 1 hour with 0.8 pbw of methacrylic anhydride and 0.001 pbw of 4-dimethylaminopyridine. Water was then added to the mixture and the product filtered off and dried.

APPLICATION EXAMPLES

Example 1

The following two coating solutions were prepared from:

52 pbw of a terpolymer of styrene, methacrylic acid and n-hexyl methacrylate (10:30:60; acid number 190), 17.6 pbw of polyethylene glycol-400-dimethacrylate 0.04 pbw of a blue azo dyestuff obtained by coupling 2,4-dinitro-6-chlorobenzenediazonium salt with 2-methoxy-5-acetylamino-N,N-diethylaniline, 0.12 pbw of 1,4-bis(4-tert-butoxyphenylamino)5,8-dihydroxyanthraquinone,
90 pbw of butanone, and
50 pbw of ethanol,
to which a) 1 pbw of 2,7-dimethyl-9-(4-methacryloylaminomethylphenyl)acridine and b) 1 pbw of 2,7-dimethyl-9-(4-acetylaminomethylphenyl)acridine (comparison)

were added as photoinitiator. A biaxially oriented and heat-set polyethylene terephthalate film having a thickness of 25 μm was coated with each of the specified solutions and dried (coating thickness in each case 100 μm). The dry resist films thus produced were then covered with a polypropylene film.

After peeling off the polypropylene top film, the resist coatings were laminated in a commercial laminating apparatus at 115° C. onto a phenolic board clad with 35 μm thick copper foil and exposed for 20 seconds with a commercial exposure apparatus (5 kW metal halide lamp). A 13-step exposure wedge having density increments of 0.15 was used as master. Then the plates were developed in a spray processor for 90 seconds with 1.0%-strength soda solution. Both resists were cured up to step 8.

The hardness of the coating was then determined on samples exposed over the entire area. For this purpose, use was made of the Buchholz indentation hardness test described in DIN 53 153. In this test the penetration of a circular knife into the coating to be tested under a defined load is measured by means of a suitable apparatus. This produces an indentation which is the deeper, the softer the material to be tested was. The value $$\frac{100}{\text{penetration depth in mm}}$$

is stated as the hardness number.

The sample according to the invention had a Buchholz hardness of 81 and the comparison sample a hardness of 72.

EXAMPLE 2 a) 1.2 pbw of 2,7-bis(α-acryloyloxybenzyl)-9-phenylacridine and b) 1.2 pbw of 2,7-bis(α-acetoxybenzyl)-9-phenylacridine (comparison)

were dissolved as photoinitiators in coating solutions composed of 40 pbw of a copolymer of methyl methacrylate and methacrylic acid (acid number 115),
40 pbw of trimethylolpropane triacrylate and
0.5 pbw of the dyestuff Disperse Blue 134 (C.I. 61 551) in
520 pbw of 2-methoxyethanol.

The solutions were applied by spinning to electrolytically roughened and anodized 0.3 mm thick aluminum. The coating was dried for 2 minutes at 100° C., a coating weight of 2.4 g/m² being obtained. Then the panels were provided with a polyvinyl alcohol top coating of 4 g/m².

The printing plates thus obtained were exposed for 15 seconds with a 5 kW metal halide lamp at a distance of 110 cm under a negative test master together with a 13-step exposure wedge which contained density increments of 0.15. The parts not cured by light were removed by wiping over with a developer solution with the following composition:

3 pbw of sodium metasilicate nonahydrate,
0.05 pbw of strontium chloride,
0.03 pbw of nonionogenic wetting agent (coconut alcohol polyoxyethylene ether containing approx. 8 oxyethylene units),
0 003 pbw of antifoaming agent,
100 pbw of demineralized water.

The printing plates were then clamped alongside each other in an offset printing press and tested under intensified conditions (doubled contact pressure between rubber blanket and printing plate using a particularly abrasive printing ink). The printing results of plate 2 b declined from 70,000 onwards. The ink takeup of plate 2 b was considerably reduced at a run of 80,000, but the impressions produced by plate 2 a were still first-class.

EXAMPLE 3

A coating solution composed of:
40 pbw of the terpolymer specified in Example 1,
40 pbw of the diurethane formed from 1 mol of 2,2,4-trimethylhexamethylenediisocyanate and 2 mol of 2-hydroxyethyl methacrylate,
0.04 pbw of 1,4-bis(4-tert-butoxyphenylamino)-5,8-dihydroxyanthraquinone,
0.75 pbw of leuco crystal violet,
0.5 pbw of 3-(4-methacryloyloxybenzylidene)-9-phenyl-2,3-dihydro-1H-cyclopenta[b]quinoline and
0.6 pbw of 2,2-dibromomalonamide in
90 pbw of butanone and
50 pbw of ethanol was applied to a 25 μm thick polyethylene terephthalate film. This was then dried for 2 minutes at 100° C. in a drying oven. A dry resist was obtained which had a coating weight of 44 g/m² and was well suited for etching processes and electroplating applications.

What is claimed is:

1. A photopolymerizable mixture which comprises:
a) a polymeric binder,
b) a polymerizable compound having at least one terminal olefinic double bond and a boiling point above 100° C. at normal pressure, and
c) a N-heterocyclic compound as photoinitiator, wherein the N-heterocyclic compound is a compound of the general formula I

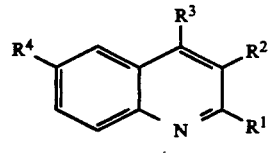

in which
$R^1$ is a group of the formula

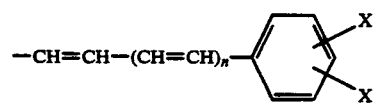

and
$R^2$ is a hydrogen atom or a methly group, or
$R^1$ and $R^2$ jointly form an unsubstituted or substituted 5- or 6-membered carbocyclic ring,
$R^3$ is a hydrogen atom, a methyl group or an unsubstituted or substituted phenyl group, $R^4$ is a hydrogen or halogen atom, a methyl group, an unsubstituted or substituted benzoyl group or a group of the formula

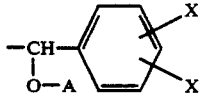

n is zero or 1,

X is a hydrogen or chlorine atom, an alkyl group containing 1 to 4 carbon atoms or one of the groups OA, $CH_2OA$, $CH_2NHA$ or $C_2H_4OA$, where a plurality of Xs may be identical or different form one another, and A is an acryloyl or methacryloyl group, the compound containing at least one group A.

2. A photopolymerizable mixture as claimed in claim 1, wherein the binder is insoluble in water and soluble or at least swellable in aqueous alkaline solutions.

3. A photopolymerizable mixture as claimed in claim 1, wherein the polymerizable compound is an ester of acrylic or methacrylic acid with an aliphatic alcohol.

4. A photopolymerizable mixture as claimed in claim 1, comprising about 20 to 90 wt % of said binder, about 10 to 80 wt % of said polymerizable compound and about 0.01 to 10 wt % of said photoinitiator, based on the nonvolatile constituents of the mixture.

5. A photopolymerizable mixture as claimed in claim 4, comprising 40 to 80 wt % of said binder, 20 to 60 wt % of said polymerizable compound and 0.1 to 5 wt % of said photoinitiator, based on the nonvolatile constituents of the mixture.

6. A photopolymerizable mixture as claimed in claim 1, consisting essentially of the recited ingredients.

7. A photopolymerizable copying material comprising a coating base and a photopolymerizable coating, wherein said coating comprises a mixture as claimed in claim 1.

8. A photopolymerizable copying material as claimed in claim 7, further comprising a top coat having a low oxygen permeability disposed on said coating.

9. A compound of the general formula I

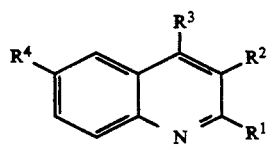

in which $R^1$ and $R^2$ jointly form an aromatic or partially hydrogenated ring.

$R^3$ is a hydrogen atom, a methyl group or an unsubstituted or substituted phenyl group, $R^4$ is a hydrogen or halogen atom, a methyl group, an unsubstituted or substituted benzoyl group or a group of the formula

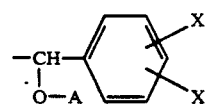

n is zero or 1,

X is a hydrogen or chlorine atom, an alkyl group containing 1 to 4 carbon atoms or one of the groups OA, $CH_2OA$, $CH_2NHA$ or $C_2H_4OA$, where a plurality of Xs may be identical or different form one another, and is an acryloyl or methacryloyl group, the compound containing at least one group A.

10. A compound as claimed in claim 9, wherein $R^1$ and $R^2$ jointly form a benzene ring.

11. A compound as claimed in claim 10, wherein the benzene ring jointly formed by $R^1$ and $R^2$ carries at least one substituent having the meaning of $R^4$.

12. A compound as claimed in claim 11, wherein the substituent $R^4$ is in the 2-position of the acridine nucleus formed with said benzene ring jointly formed by $R^1$ and $R^2$.

13. A compound of the general formula I

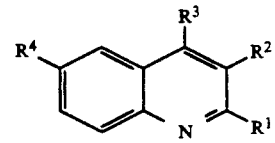

in which $R^1$ is a group of the formula

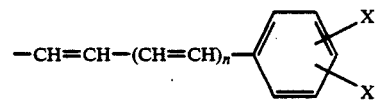

$R^2$ is a hydrogen atom or a methly group, or $R^1$ and $R^2$ jointly form an unsubstituted or substituted 5- or 6-membered carbocyclic ring, $R^3$ is a phenyl group which carries at least one substitute X.

$R^4$ is a hydrogen or halogen atom, a methyl group, an unsubstituted or substituted benzoyl group or a group of the formula

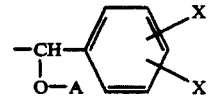

n is zero or 1,

X is a hydrogen or chlorine atom, an alkyl group containing 1 to 4 carbon atoms or one of the groups OA, $CH_2OA$, $CH_2NHA$ or $C_2H_4OA$, where a plurality of Xs may be identical or different form one another, and A is an acryloyl or methacryloyl group, the compound containing at least one group A.

* * * * *

UNITED STATES PATENT AND TRADEMARK OFFICE
CERTIFICATE OF CORRECTION

PATENT NO. : 5,200,299
DATED : April 6, 1993
INVENTOR(S) : STEPPAN et al.

It is certified that error appears in the above-indentified patent and that said Letters Patent is hereby corrected as shown below:

Column 10, line 13, claim 9, before --is-- insert "A".

Signed and Sealed this

Twenty-eighth Day of June, 1994

*Attest:*

BRUCE LEHMAN

*Attesting Officer*     *Commissioner of Patents and Trademarks*